(12) United States Patent
Nozaki et al.

(10) Patent No.: US 7,868,206 B2
(45) Date of Patent: Jan. 11, 2011

(54) TRIHALOMETHIONINE DERIVATIVE AND PHARMACEUTICAL PRODUCT CONTAINING THE SAME

(75) Inventors: Tomoyoshi Nozaki, Tokyo (JP); Takeshi Toru, Nagoya (JP); Norio Shibata, Nagoya (JP); Masaichi Yamamoto, Tokyo (JP)

(73) Assignees: National University Corporation, Gunma University, Maebashi-shi, Gunma (JP); National University Corporation, Nagoya Institute of Technology, Nagoya-shi, Aichi (JP); Arigen Pharmaceuticals, Inc., Minato-ku, Tokyo (JP)

( * ) Notice: Subject to any disclaimer, the term of this patent is extended or adjusted under 35 U.S.C. 154(b) by 391 days.

(21) Appl. No.: 12/159,459

(22) PCT Filed: Dec. 27, 2006

(86) PCT No.: PCT/JP2006/326067

§ 371 (c)(1),
(2), (4) Date: Jun. 27, 2008

(87) PCT Pub. No.: WO2007/077876

PCT Pub. Date: Jul. 12, 2007

(65) Prior Publication Data

US 2010/0076224 A1 Mar. 25, 2010

(30) Foreign Application Priority Data

Dec. 27, 2005 (JP) ............................. 2005-375453

(51) Int. Cl.
C07C 233/05 (2006.01)
A61K 31/16 (2006.01)
(52) U.S. Cl. .................... 564/194; 564/198; 514/626
(58) Field of Classification Search ................. 564/194, 564/198; 514/626
See application file for complete search history.

(56) References Cited

U.S. PATENT DOCUMENTS 5,585,519 A 12/1996 Zeller
2001/0037038 A1 11/2001 Ponceblanc et al.

FOREIGN PATENT DOCUMENTS

| JP | 7-503705 | 4/1995 |
| JP | 10-504522 | 5/1998 |
| JP | 2003-522815 | 7/2003 |
| WO | WO 93/08816 | 5/1993 |
| WO | WO 2004/078349 | 9/2004 |

OTHER PUBLICATIONS

RN 143673-85-2, 1992.*

Houston Jr., et al. "Syntheses of and Chemotactic Responses Elicited by fMET-LEU-PHE Analogs Containing Difluoro- and Trifluoromethionine," *Bioorganic & Medicinal Chemistry Letters*, vol. 7, No. 23, pp. 3007-3012, 1997.
Seko, et al. "Structure—Activity Study of L-Amino Acid-Based N-Type Calcium Channel Blockers," *Bioorganic & Medicinal Chemistry*, vol. 11, pp. 1901-1913, 2003.
International Search Report dated Mar. 6, 2007.

* cited by examiner

*Primary Examiner*—Shailendra Kumar
(74) *Attorney, Agent, or Firm*—Knobbe, Martens, Olson & Bear, LLP

(57) ABSTRACT

A compound represented by the formula (I) is used as an active ingredient in a medicament for treatment or prevention of infectious diseases caused by protozoa or bacterium.

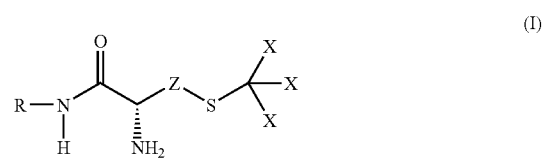

X represents halogen, Z represents —$(CH_2)_m$— wherein m is an integer of 1-5, and R represents one of the following (i)-(v):
(i) hydrogen

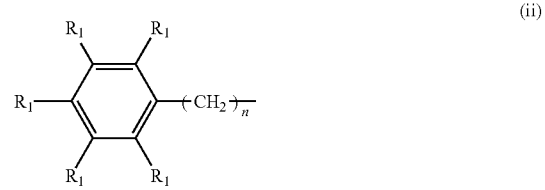

n represents an integer of 0-5, $R_1$'s independently represent hydrogen, halogen, alkoxy having 1-5 carbon atoms or alkyl having 1-5 carbon atoms.

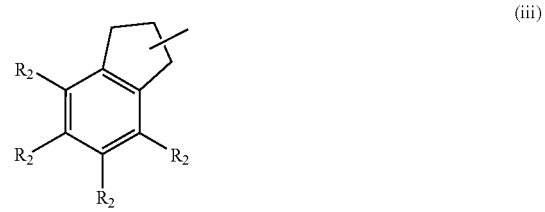

$R_2$'s independently represent hydrogen, halogen, alkoxy having 1-5 carbon atoms or alkyl having 1-5 carbon atoms.
(iv) alkyl having 1-5 carbon atoms,
(v) hydroxyalkyl having 1-5 carbon atoms.

6 Claims, 1 Drawing Sheet

TRIHALOMETHIONINE DERIVATIVE AND PHARMACEUTICAL PRODUCT CONTAINING THE SAME

CROSS-REFERENCE TO RELATED APPLICATIONS

This application is the U.S. National Phase under 35 U.S.C. §371 of International Application PCT/JP2006/326067, filed Dec. 27, 2006, which was published in a non-English language, which claims priority to JP 2005-375453, filed Dec. 27, 2005.

TECHNICAL FIELD

The present invention relates to novel trihalomethionine derivatives and a medicament containing the same, which is useful as a prophylactic drug or a therapeutic drug for infectious diseases.

BACKGROUND ART

There are annually forty-eight million patients suffering from entamebiasis around the world, in particular, in tropical developing countries, and the estimated number of deaths per year is about seventy thousand. In Japan, entamebiasis is designated as a category 5 infectious disease, and 500 to 600 cases have been reported annually.

Overview of Entamebiasis

*Entamoeba histolytica* is an anaerobic or microaerophilic protozoan that is parasitic in the large intestinal tract. Infection to human is caused by ingesting a food or water contaminated with cysts. Excystation of the cysts occurs in the small intestine, and the cysts become trophozoites and reach the large intestine to form ulcerating pathogens on the mucosal surfaces of the large intestine including the rectum, sigmoid colon, cecum, and ascending colon. Not all infected subjects exhibit symptoms of the disease, and only 5 to 10% of the infected subjects are considered to exhibit symptoms of the disease. Subjects exhibiting symptoms of the disease show dysenteric symptoms such as mucous and bloody stool, diarrhea, tenesmus, aerenterectasia, and lower abdominal pain during defecation. In typical cases, patients pass mucous and bloody stool, and exacerbation and remission are repeated at intervals of several days to several weeks. In exacerbation cases, enterobrosia is caused. Extraintestinal lesions are observed in about 5% of patients exhibiting colitis symptoms. In particular, abscesses are formed in organs or tissues such as liver, lung, brain, and skin. Of those, liver abscesses are most frequently caused and are accompanied by fever with temperatures of 38 to 40° C., hypochondrial pain, nausea, vomiting, weight loss, night sweat, or generalized fatigability. When abscesses burst, lesions are formed in the peritoneum, pleura, and epicardium, resulting in severe symptoms. Trophozoites are encysted in the large intestine and discharged to feces, which are orally ingested by another person, thereby infection is established.

Problems of Entamebiasis Treatment

In general, treatment of entamebiasis is performed by oral administration of metronidazole (product name, Flagyl), which has a high therapeutic effect on symptomatic persons. However, metronidazole is absorbed well from the digestive tract but has a low killing effect on cysts in the intestinal tract, and it is not effective for group treatment of cyst carriers. In order to treat the carriers, metronidazole is used together with diloxanide furoate, which is absorbed from the digestive tract at a low efficiency. However, the killing effect on cysts is insufficient in some cases. Another problem of metronidazole is to readily cause in vitro resistance. In view of the actual state of appearance of resistant strains in another protozoan such as *Plasmodium*, it is only a matter of time before an *Entamoeba histolytica* strain resistant to metronidazole appears. In the case of Trichomonad that is an anaerobic protozoan like *Entamoeba histolytica*, a clinical strain resistant to metronidazole has been reported. Therefore, it is necessary to synthesize a novel compound having the effect of killing *Entamoeba histolytica*.

Coombs et al. and we have reported that trifluoromethionine (compound A shown below) has pesticidal activity on anaerobic protozoans such as *Entamoeba histolytica* and *Trichomonas vaginalis* (Non-patent Document 1 or 2). The pesticidal activity of trifluoromethionine on the protozoans depends on an enzyme that is present specifically in protozoan and called methionine gamma-lyase. Methionine gamma-lyase is an enzyme involved in decomposition of sulfur-containing amino acids and is not present in mammals, and therefore, the compound has selective effects for protozoans.

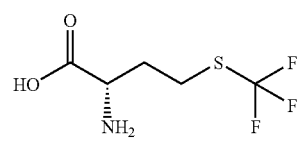

(A)

Non-patent Document 1: G. H. Coombs, J. C. Mottram, Antimicrob. Agents Chemother 2001, 45, 1743

Non-patent Document 2: M. Tokoro et al., J. Biol. Chem. 2003, 278, 42717-42727

DISCLOSURE OF THE INVENTION

An object of the present invention is to provide a pharmaceutical compound useful for treatment of infectious diseases or the like.

The inventors of the present invention made extensive studies to solve the above problems. As a result, the inventors succeeded in synthesizing novel trihalomethionine derivatives represented by the formula (I) shown below. The inventors also found that the trihalomethionine derivatives have the effect of suppressing proliferation of *Entamoeba histolytica* and therefore it can be used as a therapeutic drug or prophylactic drug for infectious diseases caused by bacteria or protozoans, thus completed the present invention.

That is, the present invention provides the compounds represented by the general formula (I),

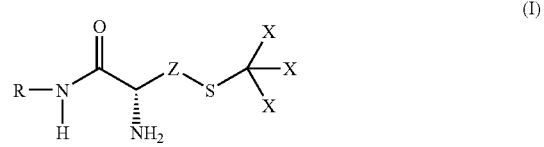

(I)

X represents halogen, Z represents —$(CH_2)_m$— in which m represents an integer of 1 to 5, and R represents one of the following (i) to (v):

(i) hydrogen;

(ii)

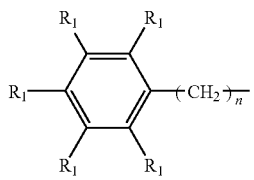

n represents an integer of 0 to 5, $R_1$'s each independently represent hydrogen, halogen, alkoxy having 1 to 5 carbon atoms, or alkyl having 1 to 5 carbon atoms;

(iii)

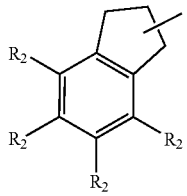

$R_2$'s each independently represent hydrogen, halogen, alkoxy having 1 to 5 carbon atoms, or alkyl having 1 to 5 carbon atoms;
(iv) alkyl having 1 to 5 carbon atoms; and
(v) hydroxyalkyl having 1 to 5 carbon atoms.

The present invention also provides a medicament comprising, as an active ingredient, the above-described compound or salt thereof.

The present invention also provides the above-described medicament, which is a therapeutic drug for an infectious disease caused by a bacterium or a protozoan.

The present invention also provides the above-described medicament, which is a therapeutic drug for entamebiasis or trichomoniasis.

The present invention also provides a method of treating an infectious disease caused by a bacterium or a protozoan, which comprises administering the compound represented by the general formula (I) to a patient.

The present invention also provides a use of the compound represented by the general formula (I) for manufacturing a therapeutic drug for an infectious disease caused by a bacterium or a protozoan.

DESCRIPTION OF THE PREFERRED EMBODIMENTS

Figure 1:
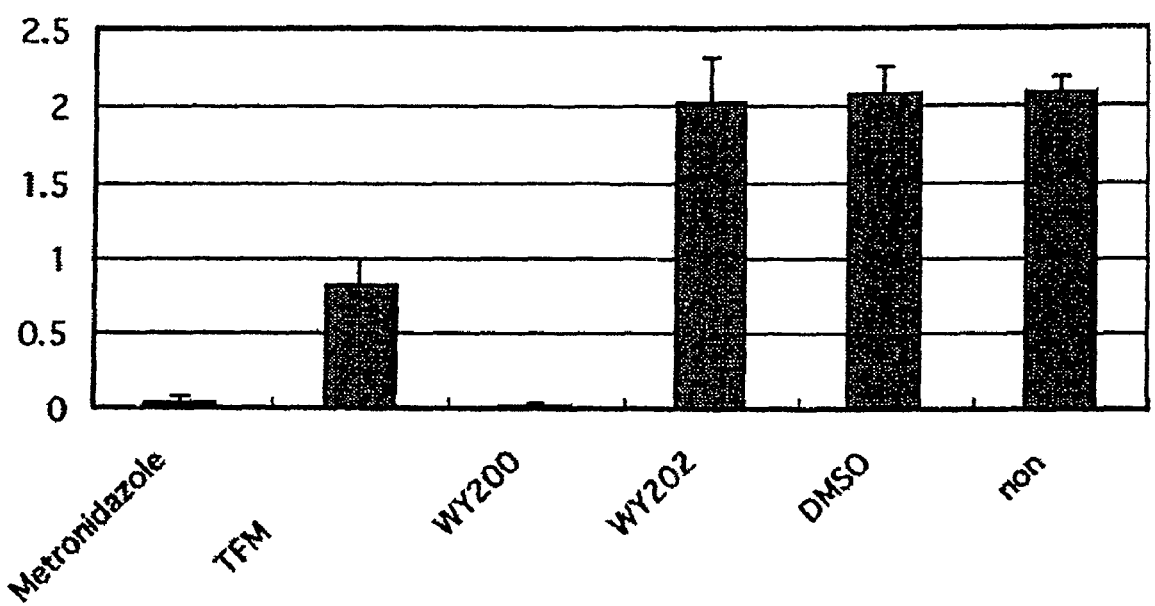
FIG. 1 is a graph showing the killing effect of each compound on an *Entamoeba histolytica* HM1:IMSS c16 strain. The vertical axis represents an arbitrary unit.

Hereinafter, the present invention will be described in detail.

<1> The trihalomethionine derivatives of the present invention have the following structural formula.

(I)

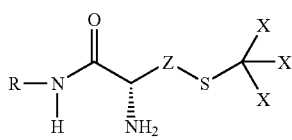

In the general formula (I), X represents halogen, preferably fluorine.

In the general formula (I), Z represents —$(CH_2)_m$— (m represents an integer of 1 to 5), more preferably —$CH_2$— or —$(CH_2)_2$—.

In the general formula (I), R represents one of the following (i) to (v).

(i) hydrogen (ii)

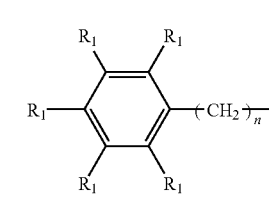

In this formula, n represents an integer of 0 to 5 (preferably 0 or 1), and $R_1$'s each independently represent a group selected from hydrogen, halogen, alkoxy having 1 to 5 carbon atoms, and alkyl having 1 to 5 carbon atoms, more preferably each independently represent a group selected from hydrogen, halogen, and alkoxy having 1 to 5 carbon atoms. Examples of the halogen include chlorine, fluorine, bromine, and iodine, and bromine or fluorine is preferable. Examples of the alkoxy having 1 to 5 carbon atoms include methoxy, ethoxy, and propoxy, and methoxy is preferable. Examples of the alkyl having 1 to 5 carbon atoms include methyl, ethyl, and propyl. In the case where $R_1$'s represent the above-described substituents other than hydrogen, the positions and numbers of the substituents on the benzene ring are not particularly limited.

(iii)

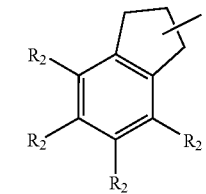

In this formula, $R_2$'S each independently represent a group selected from hydrogen, halogen, alkoxy having 1 to 5 carbon atoms, and alkyl having 1 to 5 carbon atoms, more preferably each independently represent a group selected from hydrogen, halogen, and alkoxy having 1 to 5 carbon atoms. Examples of the halogen include chlorine, fluorine, bromine, and iodine, and bromine or fluorine is preferable. Examples of the alkoxy having 1 to 5 carbon atoms include methoxy, ethoxy, and propoxy, and methoxy is more preferable. Examples of the alkyl having 1 to 5 carbon atoms include methyl, ethyl, and propyl. In the case where $R_2$'s represent the above-described substituents other than hydrogen, the positions and numbers of the substituents on the benzene ring are not particularly limited.

(iv) alkyl having 1 to 5 carbon atoms
The alkyl having 1 to 5 carbon atoms may be linear or branched.
(v) hydroxyalkyl having 1 to 5 carbon atoms
The hydroxyalkyl having 1 to 5 carbon atoms may be linear or branched, and the position of the hydroxyl group is not particularly limited.

Examples of the compounds of the present invention include the following compounds. The names of the compounds used in the present description are shown in the right hand of the structural formulae.
WY-200
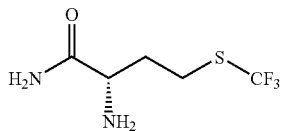
sk-258
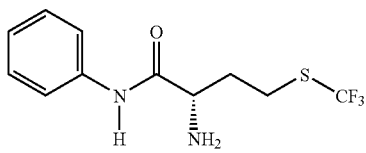
WY-241
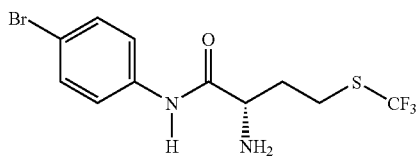
WY-242
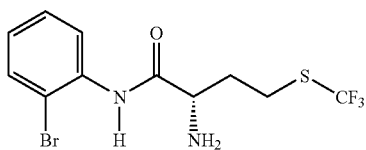
WY-244
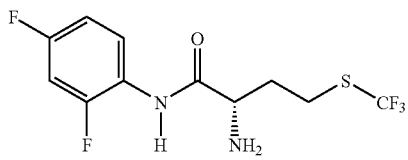
WY-246
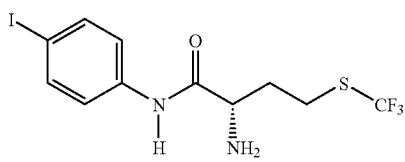
WY-252
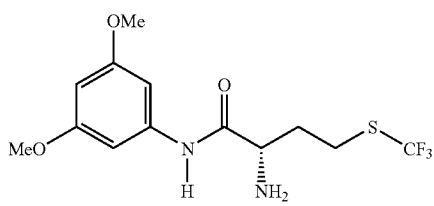
sk-337
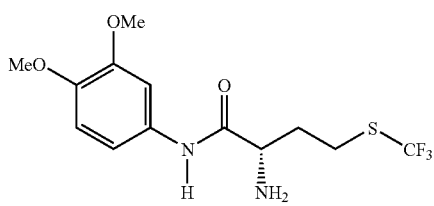
sk-336
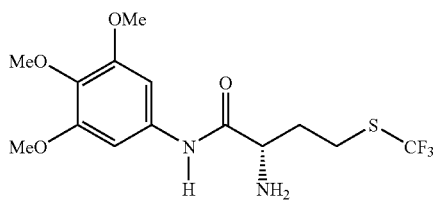
sk-328
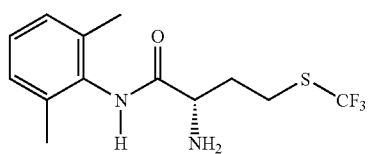
sk-281
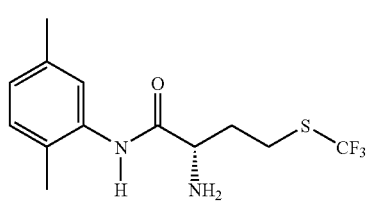
sk-329
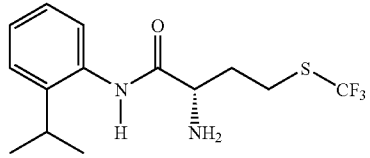
sk-332
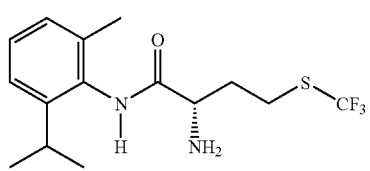
sk-344
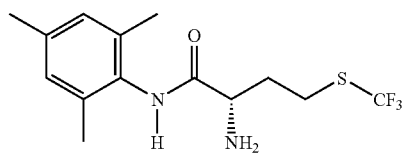
sk-338
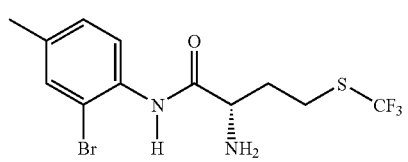
sk-278
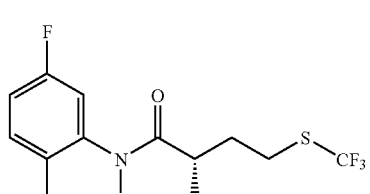
sk-254
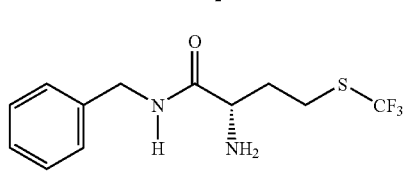

-continued

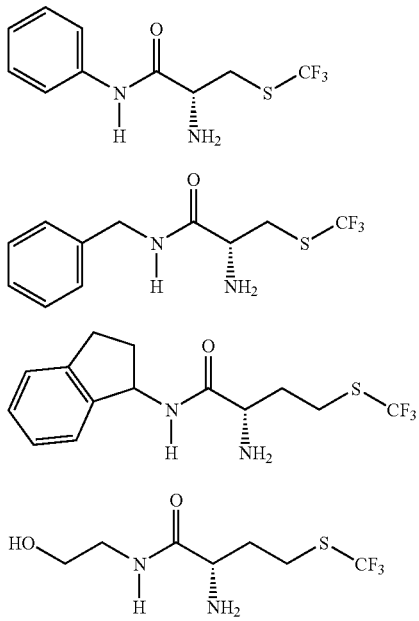

Among these compounds, WY-200, WY-241, WY-244, WY-252, sk-254, sk-258, sk-276, sk-336, sk-337, KO-10, and sk-316 are more preferable.

The compounds of the present invention can be synthesized from trifluoromethionine, for example. For example, trifluoromethionine amide(WY-200) can be obtained by: reacting trifluoromethionine with methanol to produce trifluoromethionine methyl ester; and reacting ammonia with the trifluoromethionine methyl ester.

Meanwhile, trifluoromethionine benzylamide can be obtained by reacting trifluoromethionine with benzylamine.

The trifluoromethionine to be used as a starting compound can be obtained in accordance with known methods described in the following documents.

R. L. Dannley, R. G., Taborsky, J. Org. Chem. 1957, 22, 557

M. E. Houston, J. F. Honek, J. Chem. Soc. Chem. Commun. 1989, 761

Tadashi Shiraiwa, Chem. Pharm. Bull. 2002, 50, 1081.

V. Soloshonok, V. Kukhar, Y. Pustovit, V. Nazaretian, Synlett 1992, 657.

The other compounds can be synthesized by the methods described in Examples.

The compounds represented by the formula (I) have the effect of killing a protozoan, particularly an anaerobic protozoan such as *Entamoeba histolytica* or Trichomonad, and bacteria. Therefore, the compounds can be used as a medicament for treatment (including prevention) of these protozoan or bacteria. *Entamoeba histolytica*, for example, infects not only human but also other mammals such as monkey, therefore the subject to be administered is not limited to human, and may be a mammal other than human, a reptile, or an amphibian.

The salt of the compound (I) may be used as an active ingredient of the medicament. As the salt of the compound (I), pharmacologically acceptable salt is exemplified. Examples of the salt include an acid-added salt obtained by adding an acid such as trifluoroacetate, acetic acid, lactic acid, succinic acid, maleic acid, tartaric acid, citric acid, gluconic acid, ascorbic acid, benzoic acid, methanesulfonic acid, p-toluene sulfonic acid, cinnamic acid, fumaric acid, phosphonic acid, hydrochloric acid, nitric acid, hydrobromic acid, hydroiodic acid, sulfamic acid, or sulfuric acid.

The medicament comprising, as an active ingredient, the compound represented by the formula (I) or a salt thereof can be safely administered orally or parenterally (such as topical, rectal, or intravenous administration) in the form of the compound or salt thereof as it is or as a pharmaceutical preparation obtained by mixing the compound or salt thereof with a pharmacologically acceptable carrier, such as a tablet (including a sugar-coated tablet and a film-coated tablet), powder, granule, capsule (including a soft capsule), liquid, injection, suppository, or sustained-release formulation, in accordance with a known technology generally used in a method of manufacturing a pharmaceutical preparation.

The content of the compound represented by the formula (I) in the preparation is about 0.01 to about 100% by weight based on the total weight of the preparation.

The dose of the compound represented by the formula (I) varies depending on a subject to be administered, a target organ, a symptom, an administration method, etc. and is not particularly limited, but it is generally about 0.1 to 100 mg, preferably about 1.0 to 50 mg, and more preferably about 1.0 to 20 mg per day per patient (body weight: 60 kg).

As the pharmacologically acceptable carrier, for example, an excipient, a lubricant, a binder, or a disintegrator is exemplified for a solid preparation, and a solvent, a solubilizer, a suspending agent, a tonicity adjusting agent, a buffer agent, or an analgestic agent is exemplified for a liquid preparation. In addition, general additives such as an antiseptic agent, an antioxidant, a colorant, a sweetener, an absorbent, and a moistening agent may be used in an appropriate amount, as required. Examples of the excipient include lactose, saccharose, D-mannitol, starch, cornstarch, crystalline cellulose, and light anhydrous silicic acid. Examples of the lubricant include magnesium stearate, calcium stearate, talc, and colloid silica. Examples of the binder include crystalline cellulose, saccharose, D-mannitol, dextrin, hydroxypropyl cellulose, hydroxypropyl methyl cellulose, polyvinyl pyrrolidone, starch, sucrose, gelatin, methyl cellulose, and sodium carboxymethyl cellulose. Examples of the disintegrator include starch, carboxymethyl cellulose, calcium carboxymethyl cellulose, sodium carboxymethyl starch, and L-hydroxypropyl cellulose. Examples of the solvent include water for injection, alcohol, propylene glycol, macrogol, sesame oil, corn oil, and olive oil. Examples of the solubilizer include polyethylene glycol, propylene glycol, D-mannitol, benzyl benzoate, ethanol, trisamino methane, cholesterol, triethanol amine, sodium carbonate, and sodium citrate. Examples of the suspending agent include: surfactants such as stearyl triethanol amine, sodium lauryl sulfate, lauryl aminopropionate, lecithine, benzalkonium chloride, benzethonium chloride, and glyceryl monostearate; and hydrophilic polymers such as polyvinyl alcohol, polyvinyl pyrrolidone, sodium carboxymethyl cellulose, methyl cellulose, hydroxymethyl cellulose, hydroxyethyl cellulose, and hydroxypropyl cellulose. Examples of the tonicity adjusting agent include glucose, D-sorbitol, sodium chloride, glycerin, and D-mannitol. Examples of the buffer agent include buffers such as phosphate, acetate, carbonate, and citrate. Examples of the analgestic agent include benzyl alcohol. Examples of the antiseptic agent include p-hydroxybenzoates, chlorobutanol, benzyl alcohol, phenethyl alcohol, dehydroacetate, and sorbic acid. Examples of the antioxidant include sulfite, ascorbic acid, and α-tocopherol.

The medicament of the present invention may be used with another therapeutic drug for infectious diseases in combination.

EXAMPLES

Hereinafter, the present invention will be described more specifically with reference to Examples. However, the present invention is not limited to the following Examples.

Synthesis Example 1

Synthesis of Trifluoromethionine Amide 5 ml of methanol was placed in an autoclave and cooled to −15° C., and ammonia gas was fed until methanol was saturated with the gas, to thereby prepare a solution of about 7 M ammonia in methanol. Trifluoromethionine methyl ester (50.4 mg, 0.199 mmol) was dissolved in methanol, and the solution was added to the solution of ammonia in methanol. The tube was sealed, and the mixture was stirred at 60° C. for 10 hours. The solvent was distilled off under reduced pressure, and recrystallization was performed with water, thereby 35.8 mg (89%) of trifluoromethionine amide(the general formula (II)) was obtained.

$^1$H NMR δ(D$_2$O) 2.15-2.26 (m, 2H, β-CH$_2$), 2.96 (t, 2H, J=9.0 Hz, γ-CH$_2$), 4.02 (t, 1H, J=9.0 Hz, α-CH)

$^{19}$F NMR δ-41.31 (s, CF$_3$)

IR (KBr, cm$^{-1}$): 3438, 2925, 1681, 1492, 1120, 804 mp: 165-166° C.

GCMS (m/z): 202(M$^+$), 186, 158, 115, 101, 73, 56

Synthesis Example 2

N-Boc-trifluoromethionine (sk-269)

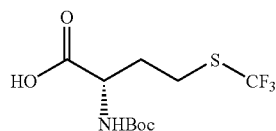

Trifluoromethionine (3.3 g, 0.016 mol) was dissolved in 1.25 N NaOH (12.7 ml), and 1,4-dioxane (9.6 ml) was further added. Boc$_2$O (3.7 g) dissolved in 1,4-dioxane (3.9 ml) was added dropwise in an ice bath. The mixture was stirred in the ice bath for 3 hours and allowed to react for 24 hours at room temperature. After completion of the reaction, 1,4-dioxane was evaporated, and 1 M KHSO$_4$ (16 ml) was added thereto, followed by extraction with ethyl acetate. The extract was washed with water (6 ml) and brine (1 ml) and dried with Na$_2$SO$_4$. The solvent was distilled off under reduced pressure, thereby the product (1.9 g, 39%) was obtained.

M.W.: 303.30

R$_f$=0.25 (hexane/ethyl acetate=60/40)

$^1$H-NMR (CDCl$_3$, 200 MHz) δ: 1.46 (9H, s), 2.05-2.12 (1H, m), 2.31-2.34 (1H, m), 2.98 (2H, t, J=7.6 Hz), 4.30-4.42 (1H, br), 8.45 (1H, br)

$^{19}$F-NMR (CDCl$_3$, 188 MHz) δ: −42.0 (s)

Synthesis Example 3

Tert-butyl (S)-1-(benzylcarbamoyl)-3-(trifluoromethylthio)ethylcarbamate (sk-242)

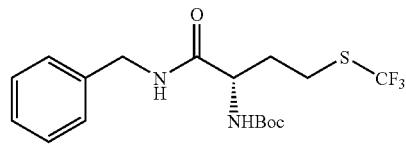

N-Boc-trifluoromethionine (200 mg, 0.659 mmol) was dissolved in 6.6 ml of dry THF in the presence of N$_2$, and the temperature was adjusted to −78° C. Subsequently, N-methylmorpholine (0.09 ml, 0.794 mmol) was added thereto, and the mixture was stirred. 2 minutes later, isobutyl chloroformate (0.10 ml, 0.794 mmol) was added thereto, and the mixture was stirred for 2 minutes. Finally, benzylamine (0.09 ml, 0.794 mmol) was added thereto. TLC was performed to confirm disappearance of the starting compound, and the solid matters were filtered, followed by distillation of THF under reduced pressure. The residue was purified by column chromatography (hexane/ethyl acetate=80/20 then 70/30), thereby the product (168.6 mg, 65%) was obtained.

$^1$H-NMR (CDCl$_3$, 200 MHz) δ: 1.42 (9H, s), 1.93-2.04 (1H, m), 2.21-2.28 (1H, m), 2.95 (2H, t, J=7.2 Hz), 4.26 (1H, br), 4.44 (2H, br), 6.44 (1H, br), 7.25 (5H, s)

$^{19}$F-NMR (CDCl$_3$, 188 MHz) δ: −41.3 (s)

Synthesis Example 4

Tert-Butyl (S)-1-(phenylcarbamoyl)-3-(trifluoromethylthio)propylcarbamate (sk-244)

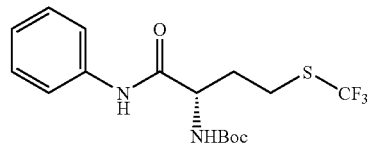

N-Boc-trifluoromethionine (200 mg, 0.659 mmol) was dissolved in 6.6 ml of dry THF in the presence of N$_2$, and the temperature was adjusted to −78° C. Subsequently, N-methylmorpholine (0.09 ml, 0.794 mmol) was added thereto, and the mixture was stirred. Two minutes later, isobutyl chloroformate (0.10 ml, 0.794 mmol) was added thereto, and the mixture was stirred for 2 minutes. Finally, aniline (0.07 ml, 0.794 mmol) was added thereto. TLC was performed to confirm disappearance of the starting compound, and the solid matters were filtered, followed by distillation of THF under reduced pressure. The residue was purified by column chromatography (hexane/ethyl acetate=80/20 then 70/30), thereby the product (168.6 mg, 65%) was obtained.

$^1$H-NMR (CDCl$_3$, 200 MHz) δ: 1.44 (9H, s), 1.94-2.20 (1H, m), 2.21-2.40 (1H, m), 3.01 (2H, t, J=7.4 Hz), 4.42 (1H, br), 7.25-7.7.49 (5H, m)

$^{19}$F-NMR (CDCl$_3$, 188 MHz) δ: −41.2 (s)

Synthesis Example 5

(S)-2-amino-N-benzyl-4-(trifluoromethylthio)butanamide hydrochloride (sk-254)

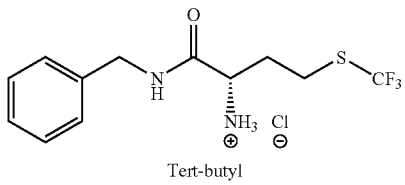

(S)-1-(benzylcarbamoyl)-3-(trifluoromethylthio)propyl-carbamate (168.8 mg, 0.430 mmol) was dissolved in 2 ml of $CH_2Cl_2$, and trifluoroacetic acid (0.32 ml, 4.296 mmol) was added dropwise in an ice bath. The mixture was stirred in the ice bath for 3 hours and allowed to react at room temperature. TLC was performed to confirm disappearance of the starting compounds, and the resultant product was dissolved in 0.1 N HCl and washed with cyclohexane three times, followed by extraction with diethyl ether three times. The aqueous layer was concentrated under reduced pressure, thereby the product (120 mg, 90%) was obtained.

$^1$H-NMR ($D_2O$, 200 MHz) δ: 2.13 (2H, q, J=7.2 Hz), 2.74-2.837 (2H, m), 3.94 (1H, t, J=6.6 Hz), 4.25 (2H, dd, J=12.2 Hz), 7.14-7.27 (5H, m)

$^{19}$F-NMR ($CDCl_3$, 188 MHz) δ: −39.5 (s)

EI Mass 292 ($M^+$HCl), 91 ($C_7H_7$), 158 ($M^+$-HCl—$C_8H_8NO$)

IR (KBr) 2977, 1668

Synthesis Example 6

(S)-2-amino-N-phenyl-4-(trifluoromethylthio)butanamide hydrochloride (sk-258)

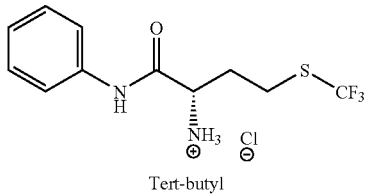

(S)-1-(phenylcarbamoyl)-3-(trifluoromethylthio)propyl-carbamate (240.2 mg, 0.635 mmol) was dissolved in 2 ml of $CH_2Cl_2$, and anisole (0.07 ml, 0.635 mmol) and trifluoroacetic acid (0.32 ml, 6.348 mmol) were separately added dropwise in an ice bath. The mixture was stirred in the ice bath for 3 hours and allowed to react at room temperature. TLC was performed to confirm disappearance of the materials, and the resultant product was dissolved in 0.1 N HCl and washed with cyclohexane three times, followed by extraction with diethyl ether three times. The aqueous layer was concentrated under reduced pressure, thereby the product (143 mg, 72%) was obtained.

$^1$H-NMR ($D_2O$, 200 MHz) δ: 2.23 (2H, q, J=8.2 Hz), 2.91 (2H, t, J=8.2 Hz) 4.10 (1H, t, J=6.4 Hz), 7.03-7.07 (1H, m), 7.16-7.30 (4H, m)

$^{19}$F-NMR ($CDCl_3$, 188 MHz) δ: −39.5 (s)

EI Mass 278 ($M^+$-HCl), 69 ($CF_3$), 77 ($C_6H_5$), 115 ($M^+$-HCl—$C_9H_{12}N_2O$), 158 ($C_4H_7F_3NS$)

IR (KBr) 3042, 1677

Synthesis Example 7

[1-(4-bromo phenylcarbamoyl-3-trifluoromethylsulfanyl-propyl]-carbamic acid tert-butyl ester (Starting Material for WY-241)

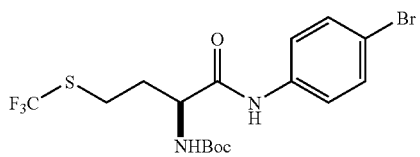

N-Boc-trifluoromethionine (253 mg, 1.016 mmol) was dissolved in dry THF in the presence of $N_2$, and the temperature was adjusted to −78° C. Subsequently, N-methylmorpholine (0.13 ml, 1.219 mmol) was added thereto, and the mixture was stirred. Two minutes later, isobutyl chloroformate (0.16 ml, 1.219 mmol) was added thereto, and the mixture was stirred for 2 minutes. Finally, 4-bromoaniline (209.7 mg, 1.219 mmol) was added thereto. TLC was performed to confirm disappearance of the starting compound, and the solid matters were filtered, followed by distillation of THF under reduced pressure. The residue was purified by column chromatography (Hex:AcOEt=80:20), thereby the product (220.3 mg, 47%) was obtained.

Molecular formula $C_{16}H_{20}BrF_3N_2O_3S$

M.W.: 457.31

$^1$H-NMR ($CDCl_3$) δ: 1.46 (9H, s), 2.03-2.12 (1H, m), 2.29-2.36 (1H, m) 3.02 (2H, t, J=7.0 Hz), 4.38 (1H, q, J=6.2 Hz), 5.10 (1H, d, J=8.4 Hz), 7.33 (4H, s), 8.42 (1H, br)

$^{19}$F-NMR ($CDCl_3$) δ: −41.8 (s)

Synthesis Example 8

1-(4-bromo phenylcarbamoyl)-3-trifluoromethylsulfanyl-propyl-ammonium chloride (WY-241)

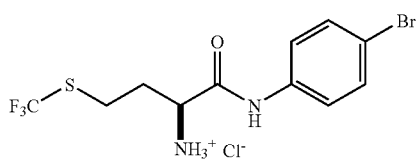

Amide WY-239 (100 mg, 0.279 mmol) was dissolved in 2 ml of methylene chloride, and anisole (0.03 ml, 0.276 mmol) and trifluoroacetic acid (0.22 ml, 2.96 mmol) were separately added dropwise in an ice bath. The mixture was stirred in the ice bath for 3 hours and allowed to react at room temperature. TLC was performed to confirm disappearance of the starting compound, and the resultant product was dissolved in 0.1 N HCl and washed with cyclohexane three times, followed by extraction with diethyl ether three times. The aqueous layer was concentrated under reduced pressure, thereby the product (75 mg, 66%) was obtained.

Molecular formula $C_{12}H_{17}BrClF_3N_2OS$
M.W.: 393.37
$^1$H-NMR ($D_2O$) δ: 2.32 (2H, q, J=6.8 Hz), 3.01 (2H, t, J=7.2 Hz), 4.14 (1H, t, J=6.4 Hz), 7.27 (2H, d, J=6.4 Hz), 7.47 (2H, d, J=6.4 Hz)
$^{19}$F-NMR ($D_2O$) δ: −42.1 (s)
IR (KBr) 2965, 1672, 1129, 683 cm$^{-1}$ Synthesis Example 9

[1-(2,4-difluoro-phenylcarbamoyl)-3-trifluoromethylsulfanyl-propyl]-carbamic acid tert-butyl ester (starting material for WY-244)

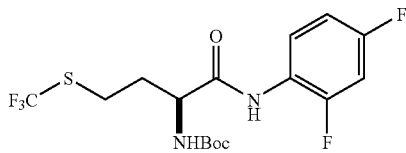

N-Boc-trifluoromethionine (212 mg, 0.851 mmol) was dissolved in dry THF in the presence of $N_2$, and the temperature was adjusted to −78° C. Subsequently, N-methylmorpholine (0.11 ml, 1.000 mmol) was added thereto, and the mixture was stirred. Two minutes later, isobutyl chloroformate (0.13 ml, 0.999 mmol) was added thereto, and the mixture was stirred for 2 minutes. Finally, 2,4-difluoroaniline (0.10 ml, 0.982 mmol) was added thereto. TLC was performed to confirm disappearance of the starting compound, and the solid matters were filtered, followed by distillation of THF under reduced pressure. The residue was purified by column chromatography (Hex:AcOEt=80:20), thereby the product (191 mg, 54%) was obtained.
Molecular formula $C_{16}H_{19}F_5N_2O_3S$
M.W.: 414.39
$^1$H-NMR (CDCl$_3$) δ: 1.46 (9H, s), 2.05-2.12 (1H, m), 2.23-2.42 (1H, m), 3.02 (2H, t, J=7.2 Hz), 4.43 (1H, q, J=7.2 Hz), 5.10 (1H, d, J=8.4 Hz), 6.85 (2H, t, J=8.4 Hz) 7.21 (2H, d, J=8.4 Hz), 8.07-8.18 (1H, m), 8.35 (1H, br,)
$^{19}$F-NMR (CDCl$_3$) δ: −41.2 (s), 113.8 (s), 124.4 (s)

Synthesis Example 10

1-(2,4-difluoro-phenylcarbamoyl)-3-trifluoromethylsulfanyl-propyl-ammonium chloride (WY-244)

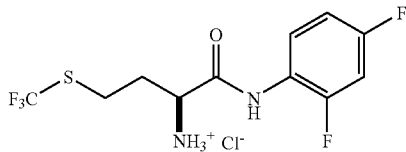

Amide WY-244 (167 mg, 0.442 mmol) was dissolved in 2 ml of methylene chloride, and anisole (0.05 ml, 0.460 mmol) and trifluoroacetic acid (0.33 ml, 4.443 mmol) were separately added dropwise in an ice bath. The mixture was stirred in the ice bath for 3 hours and allowed to react at room temperature. TLC was performed to confirm disappearance of the starring compound, and the resultant product was dissolved in 0.1 N HCl and washed with cyclohexane three times, followed by extraction with diethyl ether three times. The aqueous layer was concentrated under reduced pressure, thereby the product (90 mg, 25%) was obtained.
Molecular formula $C_{12}H_{16}ClF_5N_2OS$
M.W.: 350.70
$^1$H-NMR ($D_2O$) δ: 2.33 (2H, q, J=7.4 Hz), 3.02 (2H, t, J=7.2 Hz), 4.23 (1H, t, J=6.4 Hz), 6.92 (2H, q, J=8.4 Hz), 7.41 (1H, q, J=8.4 Hz)
$^{19}$F-NMR ($D_2O$) δ: −42.1 (s), 111.5 (t), 119.1 (d)
IR (KBr) 2914, 1694, 1508, 1114 cm$^{-1}$ Synthesis Example 11

[1-(3,5-dimethoxy-phenylcarbamoyl)-3-trifluoromethylsulfanyl-propy1]-carbamic acid tert-butyl ester (Starting Material for WY-252)

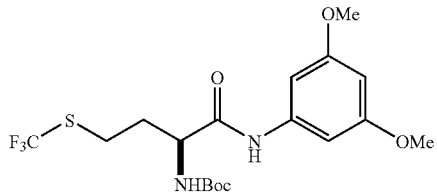

N-Boc-trifluoromethionine (189 mg, 0.758 mmol) was dissolved in dry THF in the presence of $N_2$, and the temperature was adjusted to −78° C. Subsequently, N-methylmorpholine (0.10 ml, 0.910 mmol) was added thereto, and the mixture was stirred. Two minutes later, isobutyl chloroformate (0.12 ml, 0.923 mmol) was added thereto, and the mixture was stirred for 2 minutes. Finally, 2,4-difluoroaniline (0.13 ml, 0.923 mmol) was added thereto. TLC was performed to confirm disappearance of the starting compound, and the solid matters were filtered, followed by distillation of THF under reduced pressure. The residue was purified by column chromatography (Hex:AcOEt=80:20), thereby the product (236 mg, 86%) was obtained.
Molecular formula $C_{16}H_{19}F_5N_2O_3S$
M.W.: 414.39
$^1$H-NMR (CDCl$_3$) δ: 1.46 (9H, s), 2.05-2.12 (1H, m), 2.23-2.42 (1H, m), 3.02 (2H, t, J=7.2 Hz), 4.43 (1H, q, J=7.2 Hz), 5.10 (1H, d, J=8.4 Hz), 6.85 (2H, t, J=8.4 Hz) 7.21 (2H, d, J=8.4 Hz), 8.07-8.18 (1H, m), 8.35 (1H, br,)
$^{19}$F-NMR (CDCl$_3$) δ: −41.2 (s), 113.8 (s), 124.4 (s)

Synthesis Example 12

1-(3,5-dimethoxy-phenylcarbamoyl)-3-trifluoromethylsulfanyl-propylammonium chloride (WY-252)

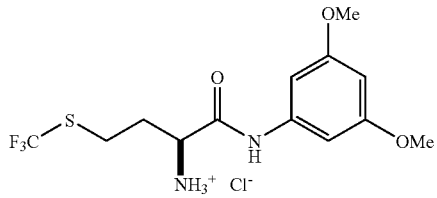

Amide WY-250 (229 mg, 0.522 mmol) was dissolved in 2 ml of methylene chloride, and anisole (0.06 ml, 0.521 mmol) and trifluoroacetic acid (0.39 ml, 5.250 mmol) were separately added dropwise in an ice bath. The mixture was stirred in the ice bath for 3 hours and allowed to react at room temperature. TLC was performed to confirm disappearance of the starting compound, and the resultant product was dissolved in 0.1 N HCl and washed with cyclohexane three times, followed by extraction with diethyl ether three times. The aqueous layer was concentrated under reduced pressure, thereby the product (132 mg, 68%) was obtained.

Molecular formula $C_{12}H_{16}ClF_5N_2OS$

M.W.: 350.70

$^1$H-NMR (D$_2$O) δ: 2.33 (2H, q, J=7.4 Hz), 3.02 (2H, t, J=7.2 Hz), 4.23 (1H, t, J=6.4 Hz), 6.92 (2H, q, J=8.4 Hz), 7.41 (1H, q, J=8.4 Hz)

$^{19}$F-NMR (D$_2$O) δ: −42.1 (s), 111.5 (t), 119.1 (d)

IR (KBr) 2914, 1694, 1508, 1114 cm$^{-1}$

Synthesis Example 13

Tert-Butyl (R)-1-(phenylcarbamoyl)-2-(trifluoromethylthio)ethylcarbamate (Starting Material for KO-10)

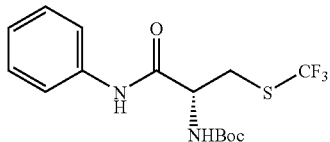

N-Boc-trifluoromethionine (200 mg, 0.691 mmol) was dissolved in 6.9 ml of dry THF in the presence of N$_2$, and the temperature was adjusted to −78° C. Subsequently, N-methylmorpholine (0.09 ml, 0.832 mmol) was added thereto, and the mixture was stirred. 2 minutes later, isobutyl chloroformate (0.11 ml, 0.832 mmol) was added thereto, and the mixture was stirred for 2 minutes. Finally, aniline (0.08 ml, 0.832 mmol) was added thereto. TLC was performed to confirm disappearance of the starting compound, and the solid matters were filtered, followed by distillation of THF under reduced pressure. The residue was purified by column chromatography (hexane/ethyl acetate=80/20 then 70/30), thereby the product (125.7 mg, 50%) was obtained.

$^1$H-NMR (CDCl$_3$, 200 MHz) δ: 1.49 (9H, s), 3.25 (1H, dd, J=6.2 Hz), 3.39 (1H, dd, J=5.8 Hz), 4.57 (q, 1H, J=8.6 Hz), 5.26 (1H, d, J=9.6 Hz), 7.09-7.51 (5H, m)

$^{19}$F-NMR (CDCl$_3$, 188 MHz) δ: −41.5 (s)

Synthesis Example 14

(S)-2-amino-N-phenyl-3-(trifluoromethylthio)propanamide hydrochloride (KO-10)

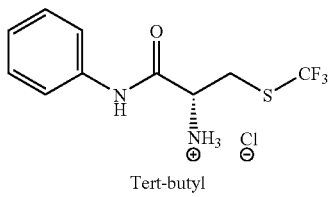

(R)-1-(phenylcarbamoyl)-2-(trifluoromethylthio)ethylcarbamate (sk-315, 125.7 mg, 0.345 mmol) was dissolved in 2 ml of CH$_2$Cl$_2$, and anisole (0.04 ml, 0.345 mmol) and trifluoroacetic acid (0.26 ml, 3.450 mmol) were separately added dropwise in an ice bath. The mixture was stirred in the ice bath for 3 hours and allowed to react at room temperature. TLC was performed to confirm disappearance of the starting compound, and the resultant product was dissolved in 0.1 N HCl and washed with cyclohexane three times, followed by extraction with diethyl ether three times. The aqueous layer was concentrated under reduced pressure, thereby the product (74.0 mg, 71%) was obtained.

$^1$H-NMR (D$_2$O, 200 MHz) δ: 3.34-3.58 (m, 2H), 4.30 (t, 1H, J=6.6 Hz), 7.08-7.35 (m, 5H)

$^{19}$F-NMR (CDCl$_3$, 188 MHz) δ: −39.7 (s)

EI Mass 264 (M$^+$-HCl), 77 (C$_6$H$_5$), 115 (M$^+$-HCl—C$_8$H$_9$N$_2$O), 144 (M$^+$-HCl—C$_7$H$_6$NO), 195 (M$^+$HCl—CF$_3$)

IR (KBr) 3468, 2971, 1673, 1604, 1556, 1496, 1450

Synthesis Example 15

Tert-Butyl (S)-1-(2,3-dihydro-1H-inden-1-ylcarbamoyl)-3-(trifluoromethylthio) propylcarbamate (Starting Material for sk-276)

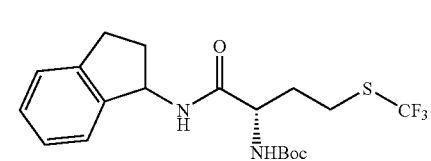

N-Boc-trifluoromethionine (200 mg, 0.659 mmol) was dissolved in 6.6 ml of dry THF in the presence of N$_2$, and the temperature was adjusted to −78° C. Subsequently, N-methylmorpholine (0.09 ml, 0.794 mmol) was added thereto, and the mixture was stirred. Two minutes later, isobutyl chloroformate (0.10 ml, 0.794 mmol) was added thereto, and the mixture was stirred for 2 minutes. Finally, 1-aminoindane (0.10 ml, 0.794 mmol) was added thereto. TLC was performed to confirm disappearance of the starting compound, and the solid matters were filtered, followed by distillation of THF under reduced pressure. The residue was purified by column chromatography (hexane/ethyl acetate=90/10 then 80/20), thereby the product (200.4 mg, 73%) was obtained.

$^1$H-NMR (CDCl$_3$, 200 MHz) δ1.41 (s, 9H), 1.73-1.84 (m, 1H), 2.04 (m, 1H), 2.25 (m, 1H), 2.55 (m, 1H), 2.97 (m, 4H), 4.24 (q, 1H, J=6.6 Hz), 5.17 (s, 1H), 5.42 (q, 1H, J=7.8 Hz), 7.21 (m, 4H)

$^{19}$F-NMR (CDCl$_3$, 188 MHz) δ: −41.3 (s)

Synthesis Example 16

(2S)-2-amino-N-(2,3-dihydro-1H-inden-1-yl)-4-(trifluoromethylthio) butanamide hydrochloride (sk-276)

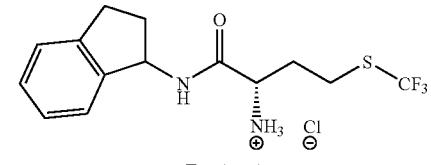

(S)-1-(2,3-dihydro-1H-inden-1-yl)-3-(trifluoromethylthio)propylcarbamate (sk-270, 200.4 mg, 0.479 mmol) was dissolved in 2 ml of $CH_2Cl_2$, and anisole (0.05 ml, 0.479 mmol) and trifluoroacetic acid (0.36 ml, 4.789 mmol) were separately added dropwise in an ice bath. The mixture was stirred in the ice bath for 3 hours and allowed to react at room temperature. TLC was performed to confirm disappearance of the starting compound, and the resultant product was dissolved in 0.1 N HCl and washed with cyclohexane three times, followed by extraction with diethyl ether three times. The aqueous layer was concentrated under reduced pressure, thereby the product (27.4 mg, 16%) was obtained.

$^1$H-NMR ($CD_3OD$, 200 MHz) δ: 1.70-1.93 (m, 1H), 2.13-2.24 (m, 2H), 2.35-2.54 (m, 1H), 2.72-2.98 (m, 4H), 3.84 (q, 1H, J=6.2 Hz), 5.32 (t, 1H, J=7.2 Hz), 7.07-7.23 (m, 4H)

$^{19}$F-NMR ($CDCl_3$, 188 MHz) δ: −40.8 (s), −40.9 (s)

EI Mass 318 ($M^+$-HCl), 69 ($CF_3$), 185 ($M^+$-HCl—$C_9H_{10}N$), 200 ($M^+$-HCl—$C_9H_9$), 216 ($M^+$-HCl—$CF_3S$)

IR (KBr): 3289, 2929, 1656, 1558

Synthesis Example 17

Tert-Butyl (R)-1-(benzylcarbamoyl)-2-(trifluoromethylthio)ethylcarbamate (Starting Material for sk-316)

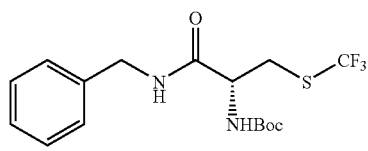

N-Boc-trifluoromethionine (200 mg, 0.691 mmol) was dissolved in 7 ml of dry THF in the presence of $N_2$, and the temperature was adjusted to −78° C. Subsequently, N-methylmorpholine (0.09 ml, 0.832 mmol) was added thereto, and the mixture was stirred. Two minutes later, isobutyl chloroformate (0.11 ml, 0.832 mmol) was added thereto, and the mixture was stirred for 2 minutes. Finally, benzylamine (0.09 ml, 0.832 mmol) was added thereto. TLC was performed to confirm disappearance of the starting compound, and the solid matters were filtered, followed by distillation of THF under reduced pressure. The residue was purified by column chromatography (hexane/ethyl acetate=80/20 then 70/30), thereby the product (169.6 mg, 65%) was obtained.

$^1$H-NMR ($CDCl_3$, 200 MHz) δ: 1.42 (9H, s), 3.21 (1H, dd, J=6.0 Hz), 3.33 (1H, dd, J=5.8 Hz), 4.43 (3H, J=6.0 Hz) (A double-triplet overlaps two doublets.), 5.22 (1H, d, J=8.8 Hz), 6.65 (1H, s), 7.24-7.37 (5H, m)

$^{19}$F-NMR ($CDCl_3$, 188 MHz) δ: −41.4 (s)

Synthesis Example 18

(R)-2-amino-N-benzyl-3-(trifluoromethylthio)propanamide hydrochloride (sk-316)

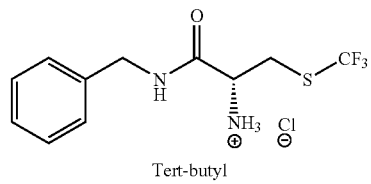

(R)-1-(benzylcarbamoyl)-2-(trifluoromethylthio)ethylcarbamate (sk-314, 169.6 mg, 0.448 mmol) was dissolved in 2 ml of $CH_2Cl_2$, and anisole (0.05 ml, 0.448 mmol) and trifluoroacetic acid (0.33 ml, 4.482 mmol) were separately added dropwise in an ice bath. The mixture was stirred in the ice bath for 3 hours and allowed to react at room temperature. TLC was performed to confirm disappearance of the starting compound, and the resultant product was dissolved in 0.1 N HCl and washed with cyclohexane three times, followed by extraction with diethyl ether three times. The aqueous layer was concentrated under reduced pressure, thereby the product (135.2 mg, 96%) was obtained.

$^1$H-NMR ($D_2O$, 200 MHz) δ: 3.31 (m, 2H), 4.12 (t, 1H, J=6.6 Hz), 4.25 (d, J=8.8 Hz), 7.13-7.22 (5H, m)

$^{19}$F-NMR ($CDCl_3$, 188 MHz) δ: −39.9 (s)

EI Mass 278 ($M^+$-HCl), 77 ($C_6H_5$), 91 ($C_7H_7$), 106 ($C_7H_8N$), 144 ($M^+$-HCl—$C_8H_8NO$), 163 ($M^+$-HCl—$C_2H_2F_3S$), 177 ($M^+$-HCl—$CF_3S$), 187 ($M^+$-HCl—$C_7H_7$)

IR (KBr) 3308, 2971, 1663, 1558, 1497, 1457

Synthesis Example 19

Tert-Butyl (S)-1-(3,4,5-trimethoxyphenylcarbamoyl)-3-(trifluoromethylthio)propylcarbamate (starting material for sk-336)

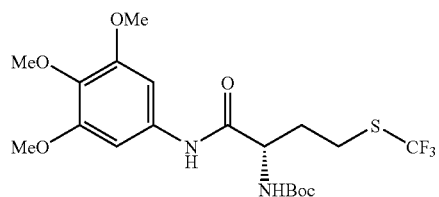

N-Boc-trifluoromethionine (208.3 mg, 0.687 mmol) was dissolved in 6.6 ml of dry THF in the presence of $N_2$, and the temperature was adjusted to −78° C. Subsequently, N-methylmorpholine (0.09 ml, 0.827 mmol) was added thereto, and the mixture was stirred. Two minutes later, isobutyl chloroformate (0.11 ml, 0.827 mmol) was added thereto, and the mixture was stirred for 2 minutes. Finally, 3,4,5-trimethoxyaniline (151.5 mg, 0.827 mmol) was added to and dissolved in 3.0 ml of THF. TLC was performed to confirm disappearance of the starting compound, and the solid matters were filtered, followed by distillation of THF under reduced pressure. The residue was purified by column chromatography (hexane/ethyl acetate=80/20 then 70/30), thereby the product (248.4 mg, 77%) was obtained.

¹H-NMR (CDCl₃, 200 MHz) δ: 1.47 (s, 9H), 1.97-2.15 (m, 1H), 2.23-2.41 (m, 1H), 3.02 (t, 2H, J=7.8 Hz), 3.78 (s, 3H), 3.81 (s, 6H), 4.40 (q, 1H, J=7.4 Hz), 5.15 (d, 1H, J=8.2 Hz), 6.76 (s, 2H), 8.43 (s, 1H) $^{13}$C-NMR (CDCl₃, 188 MHz) δ: 26.9, 28.9, 33.0, 54.7, 56.4, 61.4, 81.7, 97.6, 128.1, 133.9, 134.1, 134.8, 153.2, 156.7, 169.7

$^{19}$F-NMR (CDCl₃, 188 MHz) δ: −41.2 (s)

mp: 60.0-62.0° C.

[α]$^{20}_D$: −39.7 (c=1.000, CHCl₃)

EI Mass 468 (M⁺), 57 (C₄H₉), 69 (CF₃), 115 (C₂H₂F₃S), 158 (M⁺-C₉H₁₂NO₃—C₃H₄F₃S) 168 (C₉H₁₁O₃), 183 (C₉H₁₂NO₃), 353 (M⁺-C₂H₂F₃S), 368 (M⁺-CF₃S), 412 (M⁺-C₄H₉)

IR (KBr): 3309, 1674, 1614, 1509

Synthesis Example 20

(S)-2-amino-N-(3,4,5-trimethoxyphenyl)-4-(trifluoromethylthio)butanamide hydrochloride (sk-336)

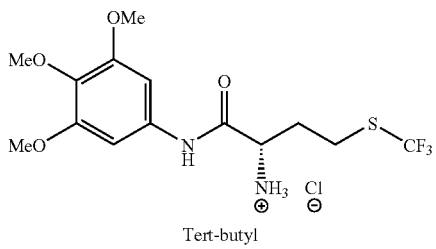

Tert-butyl (S)-1-(3,4,5-trimethoxyphenylcarbamoyl)-3-(trifluoromethylthio)propylcarbamate (sk-331, 218.7 mg, 0.467 mmol) was dissolved in 2 ml of CH₂Cl₂, and anisole (0.05 ml, 0.467 mmol) and trifluoroacetic acid (0.35 ml, 4.668 mmol) were separately added dropwise in an ice bath. The mixture was stirred in the ice bath for 3 hours and allowed to react at room temperature. TLC was performed to confirm disappearance of the starting compound, and the resultant product was dissolved in 0.1 N HCl and washed with cyclohexane three times, followed by extraction with diethyl ether three times. The aqueous layer was concentrated under reduced pressure, thereby the product (170.2 mg, 99%) was obtained.

¹H-NMR (CD₃OD, 200 MHz) δ: 2.28 (q, 2H, J=6.2 Hz), 3.02 (t, 2H, J=7.6 Hz), 3.63 (s, 3H), 3.71 (s, 6H), 4.09 (t, 1H, J=6.4 Hz), 6.91 (s, 2H)

$^{19}$F-NMR (CDCl₃, 188 MHz) δ: −40.8 (s)

EI Mass 368 (M⁺-HCl), 69 (CF₃), 115 (C₂H₂F₃S), 129 (C₃H₄F₃S), 158 (M⁺-HCl—C₁₀H₁₂NO₄), 168 (C₉H₁₁O₃), 183 (C₉H₁₂NO₃), 209 (M⁺-HCl—C₄H₇F₃NS), 267 (M⁺-HCl—CF₃S)

IR (KBr): 2944, 1690

Synthesis Example 21

Tert-Butyl (S)-1-(3,4-dimethoxyphenylcarbamoyl)-3-(trifluoromethylthio)propylcarbamate (starting material for sk-337)

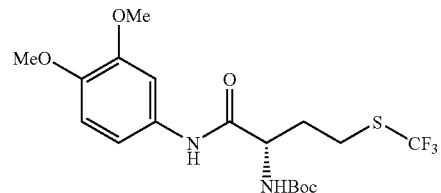

N-Boc-trifluoromethionine (200.0 mg, 0.659 mmol) was dissolved in 6.6 ml of dry THF in the presence of N₂, and the temperature was adjusted to −78° C. Subsequently, N-methylmorpholine (0.09 ml, 0.794 mmol) was added thereto, and the mixture was stirred. Two minutes later, isobutyl chloroformate (0.10 ml, 0.794 mmol) was added thereto, and the mixture was stirred for 2 minutes. Finally, 3,4-dimethoxyaniline (121.6 mg, 0.794 mmol) was added to and dissolved in 3.0 ml of THF. TLC was performed to confirm disappearance of the starting compound, and the solid matters were filtered, followed by distillation of THF under reduced pressure. The residue was purified by column chromatography (hexane/ethyl acetate=80/20 then 70/30), thereby the product (226.7 mg, 78%) was obtained.

$^{13}$C-NMR (CDCl₃, 188 MHz) δ: 26.9, 28.9, 33.2, 54.4, 56.2, 56.5, 81.4, 104.9, 111.4, 112.3, 131.3, 146.1, 149.1, 156.6, 169.7

¹H-NMR (CDCl₃, 200 MHz) δ: 1.43 (s, 9H), 2.02-2.37 (m, 2H), 2.98-3.07 (m, 2H), 3.75 (s, 3H), 3.81 (s, 3H), 4.51 (q, 1H, J=5.4 Hz), 5.59 (d, 1H, J=8.4 Hz), 6.65-6.69 (m, 1H), 6.83-6.88 (m, 1H), 7.17 (s, 1H), 8.80 (s, 1H)

$^{19}$F-NMR (CDCl₃, 188 MHz) δ: −41.2 (s)

mp: 129.5-130.0° C.

[α]$^{20}_D$: −40.7 (c=1.063, CHCl₃)

EI Mass 438 (M⁺), 57 (C₄H₉), 69 (CF₃), 138 (C₈H₉O₂), 153 (C₈H₁₀NO₂), 179 (C₉H₁₀NO₃), 338 (M⁺-CF₃S), 382 (M⁺-C₄H₉)

IR (KBr): 3303, 1665, 1612, 1516

Synthesis Example 22

(S)-2-amino-N-(3,4-dimethoxyphenyl)-4-(trifluoromethylthio)butanamide hydrochloride (sk-337)

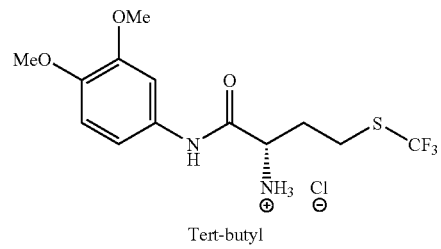

Tert-butyl (S)-1-(3,4-dimethoxyphenylcarbamoyl)-3-(trifluoromethylthio) propylcarbamate (sk-330, 196.7 mg, 0.449 mmol) was dissolved in 2 ml of CH₂Cl₂, and anisole (0.05 ml, 0.449 mmol) and trifluoroacetic acid (0.33 ml, 4.486 mmol) were separately added dropwise in an ice bath. The mixture was stirred in the ice bath for 3 hours and allowed to react at room temperature. TLC was performed to confirm disappearance of the starting compound, and the resultant product was dissolved in 0.1 N HCl and washed with cyclohexane three times, followed by extraction with diethyl ether three times. The aqueous layer was concentrated under reduced pressure, thereby the product (145.0 mg, 96%) was obtained.

$^1$H-NMR (CD$_3$OD, 200 MHz) δ: 2.27 (q, 2H, J=6.2 Hz), 3.01 (t, 2H, J=7.6

Hz), 3.71 (s, 3H), 3.72 (s, 3H), 4.03 (t, 1H, J=6.4 Hz), 6.79-6.83 (m, 1H), 6.98-7.04 (m, 1H), 7.22-7.23 (m, 1H)

$^{19}$F-NMR (CDCl$_3$, 188 MHz) δ: −40.8 (s)

EI Mass 338 (M$^+$-HCl), 69 (CF$_3$), 115 (C$_2$H$_2$F$_3$S), 129 (M$^+$-HCl—C$_3$H$_4$F$_3$S), 138 (C$_8$H$_9$O$_2$), 158 (M$^+$-HCl—C$_9$H$_{10}$NO$_3$), 181 (C$_9$H$_{10}$NO$_3$), 210 (M$^+$-HCl—C$_{10}$H$_{13}$N$_2$O$_3$) 237 (M$^+$-HCl—CF$_3$S)

IR (KBr): 2941, 1677

Example 1

Killing Effect of Trifluoromethionine Amide on *Entamoeba histolytica*

The killing effect of each of the compounds: trifluoromethionine (TFM), trifluoromethionine amide (WY200), metronidazole (known anti-amoeba drug) on an *Entamoeba histolytica* HM1: IMSS c16 strain was examined.

The *Entamoeba histolytica* HM1: IMSS c16 strain was cultured for 18 hours in a medium containing each compound at a concentration of 80 μM. FIG. 1 shows data obtained by comparing the number of cells of the HM1: IMSS c16 strain after 18 hours. The cell number was measured by determining the number of living cells of *Entamoeba histolytica* using WST-1 (Roche Diagnostics K.K.).

As a result, it was found that WY200 killed the *Entamoeba histolytica* protozoan more effectively than trifluoromethionine, further more effectively than metronidazole, which is now clinically used. Note that WY202 is another derivative of trifluoromethionine and has no anti-amoeba effect, and DMSO and none are negative control groups.

Example 2

Killing Effects of Other Compounds on *Entamoeba histolytica*

The killing effects of each of the compounds: trifluoromethionine (TFM), trifluoromethionine amide (WY200), SK254, SK258, WY241, WY244, WY252, KO10, SK276, SK316, SK336, and SK337 on *Entamoeba histolytica* HM1: IMSS c16 strain were examined. The *Entamoeba histolytica* HM1: IMSS c16 strain was anaerobically cultured in a medium containing each compound at a concentration of 0.25 to 20 μM in a 96-well plate: The number of cells after 72 hours was determined in the same way as Example 1. Table 1 shows the concentrations of the compounds required to inhibit proliferation by 50% compared to untreated controls (IC50). It was found from the results that many compounds including SK337 killed the *Entamoeba histolytica* protozoan at concentrations more than 10-fold lower than the concentration of trifluoromethionine.

TABLE 1

| Compounds | IC50 (μmol/L) |
|---|---|
| TFM | 17.2 |
| SK254 | 2.5 |
| SK258 | 2.5 |
| WY241 | 11.8 |
| WY244 | 5.5 |
| WY252 | 1.6 |
| KO10 | 13.7 |
| SK276 | 6.8 |
| SK316 | 8.9 |
| SK336 | 1.7 |
| SK337 | 1.5 |

Example 3

Therapeutic Effect of Trifluoromethionine Amide on a Hamster Liver Abscess Model Next, the compound of the present invention was evaluated in an animal infection experiment using a hamster liver abscess model.

First, an *Entamoeba histolytica* HM1: IMSS c16 strain was injected to 3-week-old female hamsters to induce liver abscesses. As is clear from the results of the control group shown in Table 2, injection of the strain caused liver abscesses and increased the total weights of the liver. On the other hand, intraperitoneal administration of 40 μmol of trifluoromethionine amide (WY200) to the hamsters caused no liver abscess and did not increase the total weights of the liver. Meanwhile, the weights of the hamsters administrated with the compound increased as steadily as the control group. Note that WY202 is another derivative of trifluoromethionine and has no anti-amoeba effect. In Table 2, A, B, and C in the respective groups show individual hamsters used.

Note that the effects of the compounds of the present invention on *Entamoeba histolytica* are shown in this Example, but it is reasonably understood that the compounds of the present invention can be effective also for a protozoan such as Trichomonad or a bacterium because trifluoromethionine or metronidazole is known to have a killing effect on Trichomonad or the like as well.

TABLE 2

| Total liver weight (mg) | Liver non-abscess portions (mg) | Liver abscess portions (mg) |
|---|---|---|
| コントロール | | |
| A. 3694 | 2094 | 1600 |
| B. 4183 | 3033 | 1150 |
| WY200 | | |
| A. 2157 | 2145 | 12 |
| B. 2814 | 2814 | 0 |
| WY202 | | |
| A. 4753 | 3230 | 1523 |
| B. 4305 | 2644 | 1661 |
| C. 5623 | 3479 | 2144 |

Example 4

Therapeutic Effect of Other Compounds in the Hamster Liver Abscess Model

Many other compounds (trifluoromethionine, SK254, SK258, WY241, WY244, and WY252) were evaluated in animal infection experiments in the same way as Example 3. The results are shown in Table 3. Intraperitoneal administration of the compounds at a concentration of 3 μmol (1.1 to 1.3 mg) per hamster (body weight 28 to 37 g) caused no liver abscess and did not increase the total weights of the liver. The animal experiments revealed that the compounds of the present invention are effective for treatment of entamebiasis.

TABLE 3

Therapeutic effects of the trihalomethionine derivatives on abscess in hamster liver
Total liver weight (mg) = Liver non-abscess portions (mg) + Liver abscess portions (mg)

| Control: | A. 3,679 | 2,863 | 816 |
|---|---|---|---|
| | B. 4,701 | 2,871 | 1,830 |
| | C. 3,511 | 2,570 | 941 |
| SK254: | A. 2,318 | 2,318 | — |
| | B. 2,193 | 2,193 | — |
| | C. 2,386 | 2,386 | — |
| SK258: | A. 2,071 | 2,071 | — |
| | B. 2,768 | 2,768 | — |
| | C. 1,510 | 1,510 | — |
| WY200: | A. 3,059 | 3,059 | — |
| | B. 1,624 | 1,624 | — |
| TFM: | A. 2,240 | 2,240 | — |
| | B. 2,415 | 2,415 | — |
| | C. 2,575 | 2,575 | — |
| WY241: | A. 2,916 | 2,916 | — |
| | B. 2,371 | 2,371 | — |
| | C. 2,900 | 2,900 | — |
| WY244: | A. 2,575 | 2,561 | 14 |
| | B. 2,181 | 2,181 | — |
| | C. 2,570 | 2,570 | — |
| WY252: | A. 2,539 | 2,1204 | 19 |
| | B. 3,338 | 3,338 | — |
| | C. 2,687 | 2,687 | — |

INDUSTRIAL APPLICABILITY

The compounds of the present invention can be used as a therapeutic drug or a prophylactic drug for infectious diseases caused by protozoans or bacteria.

What is claimed is:

1. A compound represented by the general formula (I),

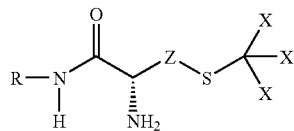

(I)

X represents halogen, Z represents $-(CH_2)_m-$ in which m represents an integer of 1 to 5, and R represents one of the following (i) to (v):

(i) hydrogen;

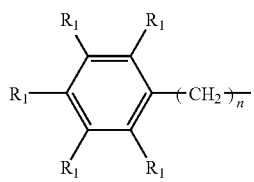

(ii)

n represents an integer of 0 to 5, $R_1$'s each independently represent hydrogen, halogen, alkoxy having 1 to 5 carbon atoms, or alkyl having 1 to 5 carbon atoms;

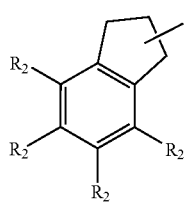

(iii)

$R_2$'s each independently represent hydrogen, halogen, alkoxy having 1 to 5 carbon atoms, or alkyl having 1 to 5 carbon atoms;

(iv) alkyl having 1 to 5 carbon atoms; and (v) hydroxyalkyl having 1 to 5 carbon atoms.

2. The compound according to claim 1, wherein R in the general formula (I) is one of the items (i) to (iii).

3. The compound according to claim 1, wherein said compound is one of the following compounds:

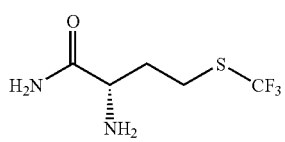

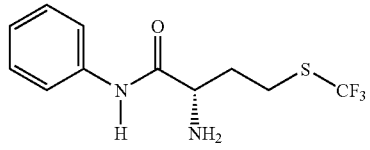

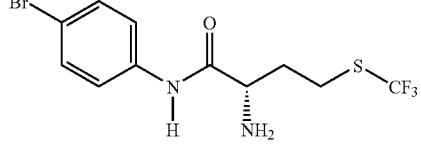

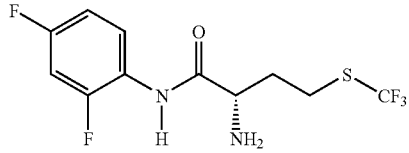

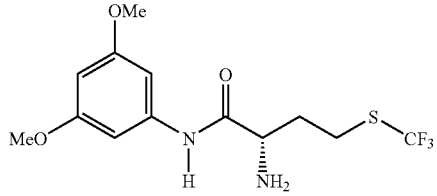

-continued
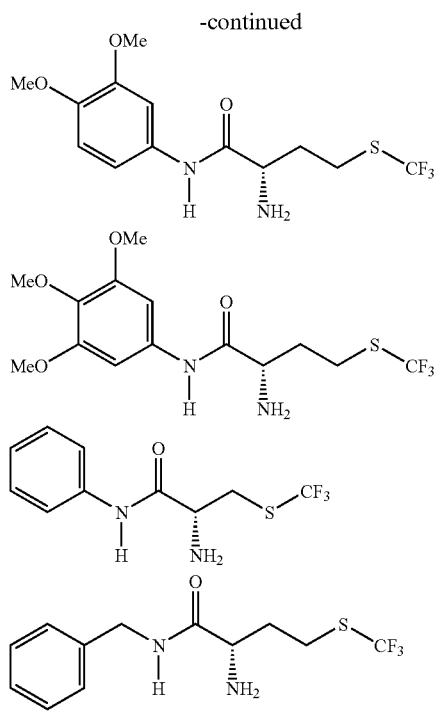
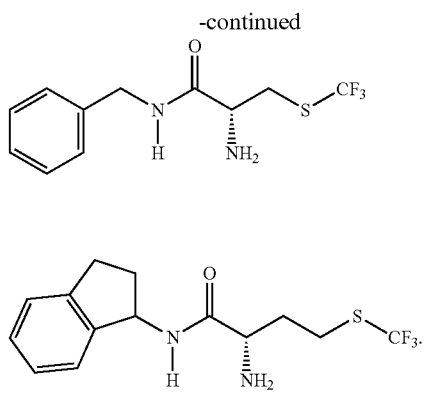
4. A medicament comprising, as an active ingredient, the compound according to any one of claims 1 to 3 or a salt thereof.
5. The medicament according to claim 4, which is a therapeutic drug for an infectious disease caused by a bacterium or a protozoan.
6. The medicament according to claim 4, which is a therapeutic drug for entamebiasis or trichomoniasis.
* * * * *